(12) United States Patent
Noy et al.

(10) Patent No.: US 7,745,856 B2
(45) Date of Patent: Jun. 29, 2010

(54) LIPID NANOTUBE OR NANOWIRE SENSOR

(75) Inventors: Aleksandr Noy, Belmont, CA (US);
Olgica Bakajin, San Leandro, CA (US);
Sonia Létant, Livermore, CA (US);
Michael Stadermann, Dublin, CA (US);
Alexander B. Artyukhin, Menlo Park, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 28 days.

(21) Appl. No.: 12/368,382

(22) Filed: Feb. 10, 2009

(65) Prior Publication Data

US 2010/0065822 A1    Mar. 18, 2010

Related U.S. Application Data

(63) Continuation of application No. 11/338,512, filed on Jan. 23, 2006, now Pat. No. 7,544,978.

(60) Provisional application No. 60/646,905, filed on Jan. 24, 2005.

(51) Int. Cl.
*H01L 29/72* (2006.01)

(52) U.S. Cl. .............................. 257/213; 257/E29.173; 977/702; 977/907

(58) Field of Classification Search ................... 257/40, 257/213; 977/702, 902; 424/450; 438/1; 530/326
See application file for complete search history.

(56) References Cited

U.S. PATENT DOCUMENTS

| | | | |
|---|---|---|---|
| 5,368,712 A * | 11/1994 | Tomich et al. | 204/403.06 |
| 6,203,864 B1 | 3/2001 | Zhang et al. | |
| 6,325,909 B1 | 12/2001 | Li et al. | |
| 6,515,325 B1 | 2/2003 | Farnworth et al. | |
| 6,613,875 B1 * | 9/2003 | Ghadiri | 530/321 |
| 6,913,697 B2 | 7/2005 | Lopez et al. | |
| 6,977,155 B2 | 12/2005 | Lahiri et al. | |
| 2002/0027312 A1 | 3/2002 | Yakobson | |
| 2003/0044608 A1 | 3/2003 | Yoshizawa et al. | |
| 2003/0098488 A1 * | 5/2003 | O'Keeffe et al. | 257/401 |
| 2003/0134433 A1 * | 7/2003 | Gabriel et al. | 436/518 |

(Continued)

FOREIGN PATENT DOCUMENTS

WO    WO 2004/031721 A2    4/2004

OTHER PUBLICATIONS

D.K. Schwartz, "Langmuir-Blodgett film structure", Surface Science Reports vol. 27, Issues 7-8, 1997, pp. 245-334.*

(Continued)

*Primary Examiner*—Thanh V Pham
*Assistant Examiner*—Jami M Valentine
(74) *Attorney, Agent, or Firm*—Eddie E. Scott; John H. Lee

(57) ABSTRACT

A sensor apparatus comprising a nanotube or nanowire, a lipid bilayer around the nanotube or nanowire, and a sensing element connected to the lipid bilayer. Also a biosensor apparatus comprising a gate electrode; a source electrode; a drain electrode; a nanotube or nanowire operatively connected to the gate electrode, the source electrode, and the drain electrode; a lipid bilayer around the nanotube or nanowire, and a sensing element connected to the lipid bilayer.

21 Claims, 3 Drawing Sheets

U.S. PATENT DOCUMENTS

| | | | |
|---|---|---|---|
| 2004/0022691 A1* | 2/2004 | Allen et al. | 422/102 |
| 2004/0023372 A1* | 2/2004 | Klein et al. | 435/317.1 |
| 2004/0253741 A1 | 12/2004 | Star et al. | |
| 2005/0037374 A1 | 2/2005 | Melker et al. | |
| 2005/0051805 A1 | 3/2005 | Kim et al. | |
| 2005/0181409 A1 | 8/2005 | Park et al. | |
| 2005/0260685 A1 | 11/2005 | Fang et al. | |

OTHER PUBLICATIONS

Richard et al, "Supra molecular Self-Assembly of Lipid Derivatives on Carbon Nanotubes", Science, 300, p. 775, May 2, 2003.*

Ji et al, "Direct Sol-Gel Replication without Catalyst in an Aqueous Gel System: From a Lipid Nanotube with a Single Bilayer Wall to a Uniform Silica Hollow Cylinder with an Ultrathin Wall", Chemistry of Materials, vol. 16, pp. 250-254, 2004 (published on Web Dec. 23, 2003).*

Katz, E., et al, "Biomolecule-functionalized Carbon Nanotubes: Applications in Nanobioelectronics," ChemPhysChem 2004, 5, pp. 1084-1104.

* cited by examiner

LIPID NANOTUBE OR NANOWIRE SENSOR

RELATED APPLICATION

This application is a continuation of U.S. patent application Ser. No. 11/338,512 filed Jan. 23, 2006 now U.S. Pat. No. 7,544,978 which claims the benefit of U.S. Provisional Patent Application No. 60/646,905 filed Jan. 24, 2005 titled "One-dimensional Lipid Bilayers on Carbon Nanotube Templates." U.S. Provisional Patent Application No. 60/646,905 filed Jan. 24, 2005 and titled "One-dimensional Lipid Bilayers on Carbon Nanotube Templates" is incorporated herein by this reference.

STATEMENT AS TO RIGHTS TO INVENTIONS MADE UNDER FEDERALLY SPONSORED RESEARCH AND DEVELOPMENT

The United States Government has rights in this invention pursuant to Contract No. W-7405-ENG-48 between the United States Department of Energy and the Lawrence Livermore National Security, LLC for the operation of Lawrence Livermore National Laboratory.

BACKGROUND

1. Field of Endeavor

The present invention relates to sensors and more particularly to a lipid nanotube or nanowire sensor.

2. State of Technology

United States Patent Application No. 2004/0253741 by Alexander Star and George Gruner for analyte detection in liquids with carbon nanotube field effect transistor devices published Dec. 16, 2004 provides the following state of technology information: "A variety of spectroscopic methods are currently used to detect analytes and monitor chemical reactions in a liquid environment. These detection methods, where electronic signal generation in response to an analyte is mediated by an optical step, are sensitive to changes in electronic configurations of the atoms and molecules involved in such reactions. Electronic detection devices with transistor configurations have also been fabricated and used for direct electronic signal generation in response to an analyte, although such techniques however have not yielded fully satisfactory alternatives to spectroscopic detection. The recent emergence of nano-scale devices offers the opportunity to effect extremely sensitive electronic detection of analytes by monitoring the electronic performance of such devices as they are exposed to a test sample environment. Field-effect transistors (FETs) fabricated using semiconducting single wall carbon nanotubes (nanotube FETs, NTFETs) and their electrical performance characteristics have been studied extensively. The conductance characteristics of carbon nanotubes have been found, for example, to be sensitive to the presence of various gases, such as oxygen and ammonia, and thus nanotubes included in an electrical circuit can operate as sensitive chemical sensors. NTFET devices, as well as nanowire-based devices, are promising candidates for the electronic detection of biological species. The mechanism of the electrical responsiveness of these devices to the presence of analytes occurs through transfer of charge between the analyte and the nanotube conducting channel, as evidenced by experiments involving electron donating ($NH_3$) and electron withdrawing ($NO_2$) molecules in gas phase. Such nanotube-based devices have also been configured in such a way that the gate electrode is provided by a buffer, in this configuration these devices can be used as pH sensors."

United States Patent Application No. 2005/0051805 by Byong Man Kim, et al for microprocessors with improved power efficiency published Mar. 10, 2005 provides the following state of technology information: "Nanotubes comprise nanometer scale tubular structures, typically made from a sheet of carbon atoms known as a graphene. They may be single wall or multi-wall structures. A single-walled carbon nanotube typically comprises an elongated, single hollow tube that is about 1 nm in diameter and few-hundreds-nm to few-hundreds-µm in length. A multi-walled carbon nanotube consists of a plurality of generally concentric, hollow tubes of different diameters that can range up to a few hundreds of nanometers. One popular method of synthesizing high quality carbon-nanotube structures uses a chemical vapour deposition technique based on a vapour-solid interaction of methane and hydrogen with a catalyst in a heated environment, as described by J. Kong, H. T. Soh, A. Cassell, C. F. Quate, H. Dai, Nature, 395, 878 (1998). A carbon-nanotube structure can act as a semiconductor or a metal, depending on its diameter and how it is rolled up from a sheet of graphene, and has been demonstrated to be harder than the steel and a better conductor than copper. Reference is directed to P. McEuen, M. Fuhrer, H. Park, IEEE Transactions on Nanotechnology, 1, 78 (2002). Various devices have been formed from carbon-nanotube structures. Ballistic conduction in nanotube structures has been reported where nanotubes placed between ferromagnetic contacts were used to demonstrate coherent transport of electron spin, as described by K. Tsukagoshi, B. Alphenaar and H. Ago, Nature, 401, 572 (1999). There have been a number of reports on the use of nanotube structures as the channel material of transistors which performed better than state of the art CMOS or SOI prototypes and reference is directed to S. Tans, A. Verschueren, and C. Dekker, Nature, 393, 49 (1998); R. Martel et al., Appl. Phys. Lett., 73, 2447 (1998); and A. Javey et al., Nature Materials, published online: 17 Nov. 2002; doi:10. 1038/nmat769. Logic functions have also been demonstrated from assembly of nanotube transistors, as described in V. Derycke, Nano Letters, 1, 453 (2001) and A. Bachtold et al., Science, 294, 1317 (2001). A single electron memory was demonstrated in which a nanotube channel of a transistor was used as a single electron sensor and manipulator—see M. Fuhrer et al., Nano Letters, 2, 755 (2002). Also, a nanotube channel of a transistor has been used as an IR source, in which the IR emission was achieved by recombining electrons and holes in the nanotube channel, injected from the source and drain of the transistor, as reported by J. A. Misewich et al., Science 300, 783 (2003). The structures described so far are demonstration devices and not apt to yield consistent device characteristics. Various methods of forming heterojunctions in carbon-nanotube structures have been proposed in an attempt to produce more reliable devices. Heterojunctions formed by adjoining carbon-nanotubes of differently rolled-up layers of closely packed carbon atoms of different diameters have been proposed in U.S. Pat. No. 6,538,262 to V. Crespi et al. Structures utilizing mechanical deformation i.e., by straining or bending are described in U.S. patent application Ser. No. 20020027312 A1, Mar. 7, 2002. Chemical doping of carbon-nanotube structures has been proposed by C. Zhou, Science, 290, 1552 (2000) to B. Yakobson. Also, a method of forming a heterojunction in a nanotube structure by means of a heat induced solid-solid diffusion and chemical reaction is described in U.S. Pat. No. 6,203,864 to Y. Zhang and S. Iijima. However, these junction forming techniques are not particularly suited to forming transistor structures. U.S. patent application Ser. No. 20030044608 A1 by H. Yoshizawa discloses a number of nanotube structures in which an outer graphene sheet is chemically modified to change its conductive characteristics, but the resulting structure does not exhibit a transistor action. It has been proposed to use Y-shaped nanotube structures to form transistors as described in U.S. Pat. No. 6,325,909 to J. Li et al. The transistor action results from heterojunctions formed by structural defects in the vicinity of the confluence of the arms of the Y-shaped nanotube and so the device lacks reproducibility. Also, transistors comprising vertically extending nanotube structures have been proposed in U.S. Pat. No. 6,515,325 to W. Farnworth, and U.S. Pat. No. 6,566,704 to W. Choi et al. However, vertical nanotube structures are known to include a high density of various defects and exhibit poor semiconductor properties, degrading performance of the transistor."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

Microfluidics is a multidisciplinary field comprising physics, chemistry, engineering, and biotechnology that studies the behavior of fluids at the microscale and mesoscale, that is, fluids at volumes thousands of times smaller than a common droplet. It is a new science, having emerged only in the 1990s, so the number of applications for this technology is currently small. However, it is potentially significant in a wide range of technologies. Microfluidics is used in the development of DNA microarray technology, micro-thermal and micro-propulsion technologies, and lab-on-a-chip technology. Microfluidics also concerns the design of systems in which such small volumes of fluids will be used. The behavior of fluids at the microscale can differ from 'macrofluidic' behavior in that factors such as surface tension, energy dissipation, and electrokinetics start to dominate the system. Microfluidics studies how these behaviors change, and how they can be worked around, or exploited for new uses. A microfluidic device can be identified by the fact that it has one or more channels with at least one dimension less than 1 mm.

Nanowires and nanotubes provide a critical enabling technology for chem/bio sensing. Their surface-to-volume ratio is phenomenally high; therefore, surface events such as binding of a protein or an ion can trigger a significant change in bulk electronic properties and enable electrical detection of binding events.

The present invention provides a sensor apparatus comprising a nanotube or nanowire, a lipid bilayer around the nanotube or nanowire, and a sensing element connected to the lipid bilayer. The present invention also provides a biosensor apparatus comprising a gate electrode; a source electrode; a drain electrode; a nanotube or nanowire operatively connected to the gate electrode, the source electrode, and the drain electrode; a lipid bilayer around the nanotube or nanowire, and a sensing element connected to the lipid bilayer.

The lipid bilayer nanotube or nanowire sensor can detect variations in ion transport through a protein pore using the lipid bilayer nanotube or nanowire sensor. The lipid bilayer nanotube or nanowire biosensor provide superior detection efficiency by using signal amplification, and also permit straightforward integration and multiplexing. The lipid bilayer nanotube or nanowire biosensor also provide a large amount of flexibility allowing seamless integration with different types of membrane-based sensing agents. The lipid bilayer nanotube or nanowire sensor and the biosensor device feature high selectivity, low cost and low power consumption, and can serve as a wearable "bio-smoke alarm."

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
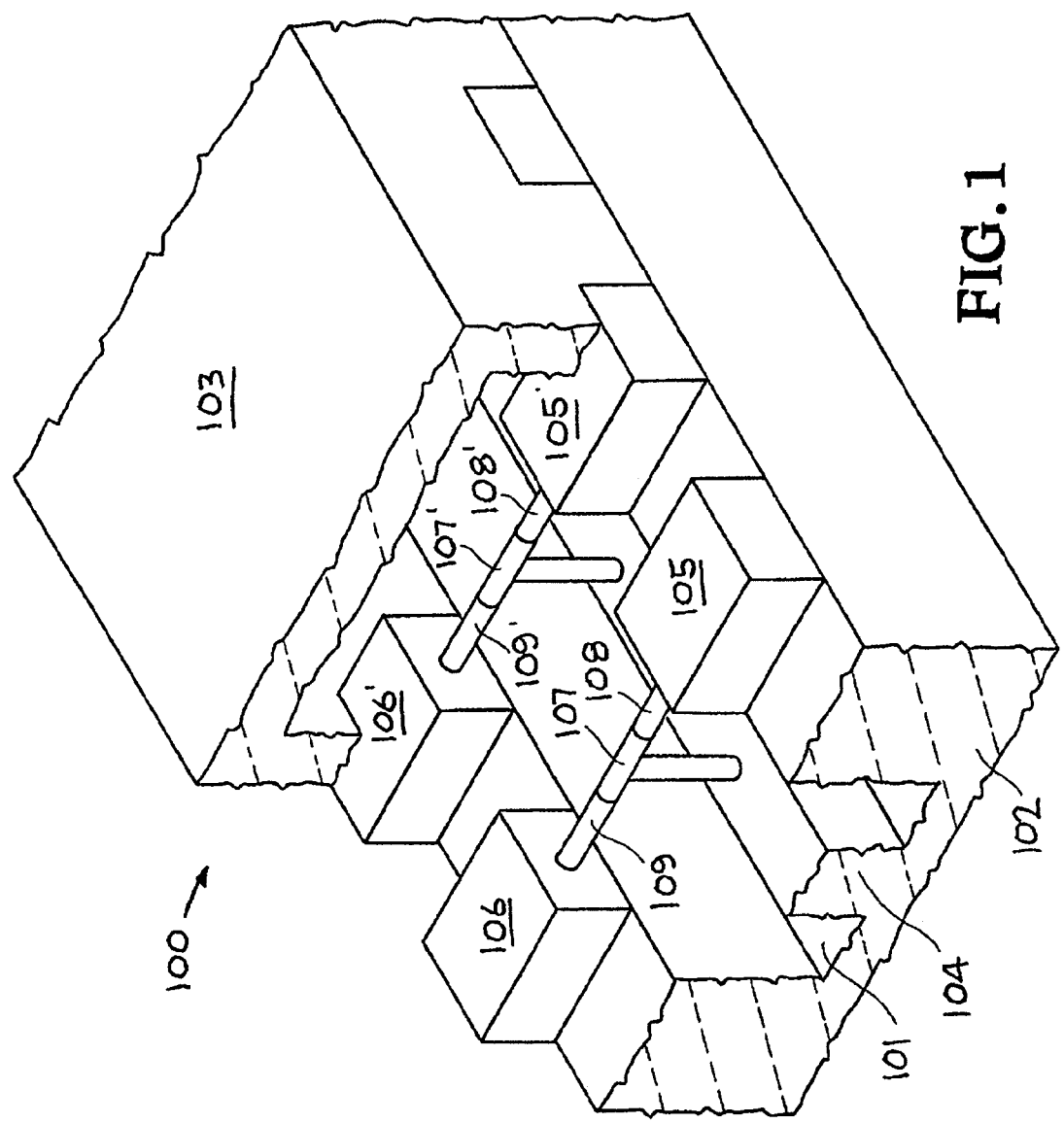
FIG. 1 illustrates one embodiment of a microfluidic device constructed in accordance with the present invention.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Referring now to FIG. 1, one embodiment of a microfluidic device constructed in accordance with the present invention is illustrated. The microfluidic device system is designated generally by the reference numeral 100. Microfluidics is a multidisciplinary field comprising physics, chemistry, engineering and biotechnology that studies the behavior of fluids at the microscale and mesoscale; that is, fluids at volumes thousands of times smaller than a common droplet. It is a new science, having emerged only in the 1990s, so the number of applications for this technology is currently small. However, it is potentially significant in a wide range of technologies. Microfluidics is used in the development of DNA microarray technology, micro-thermal and micro-propulsion technologies, and lab-on-a-chip technology. Microfluidics also concerns the design of systems in which such small volumes of fluids will be used. The behavior of fluids at the microscale can differ from 'macrofluidic' behavior in that factors such as surface tension, energy dissipation, and electrokinetics start to dominate the system. Microfluidics studies how these behaviors change, and how they can be worked around, or exploited for new uses. A microfluidic device can be identified by the fact that it has one or more channels with at least one dimension less than 1 mm.

Nanowires and nanotubes provide a critical enabling technology for chem/bio sensing. Their surface-to-volume ratio is phenomenally high, therefore surface events such as binding of a protein or an ion can trigger a significant change in bulk electronic properties and enable electrical detection of binding events.

The microfluidic device 100 includes a PDMS microfluidic channel 101 formed in a base 102. An upper section 103 covers the PDMS microfluidic channel 101. A gate 104, a source 105, and a drain 106 are located in the PDMS microfluidic channel 101. A lipid bilayer-carbon nanotube transistor 107 is connected to the gate 104, source 105, and drain 106 by connectors 108 and 109.

Additional lipid bilayer-carbon nanotube transistors can be included in the system 100 to provide an array of nanotube transistors. For example, the system 100 also includes a lipid bilayer-carbon nanotube transistor 107'. The lipid bilayer-carbon nanotube transistor 107' is connected to the gate 104, a source 105', and a drain 106' by connectors 108' and 109'.

Figure 2:
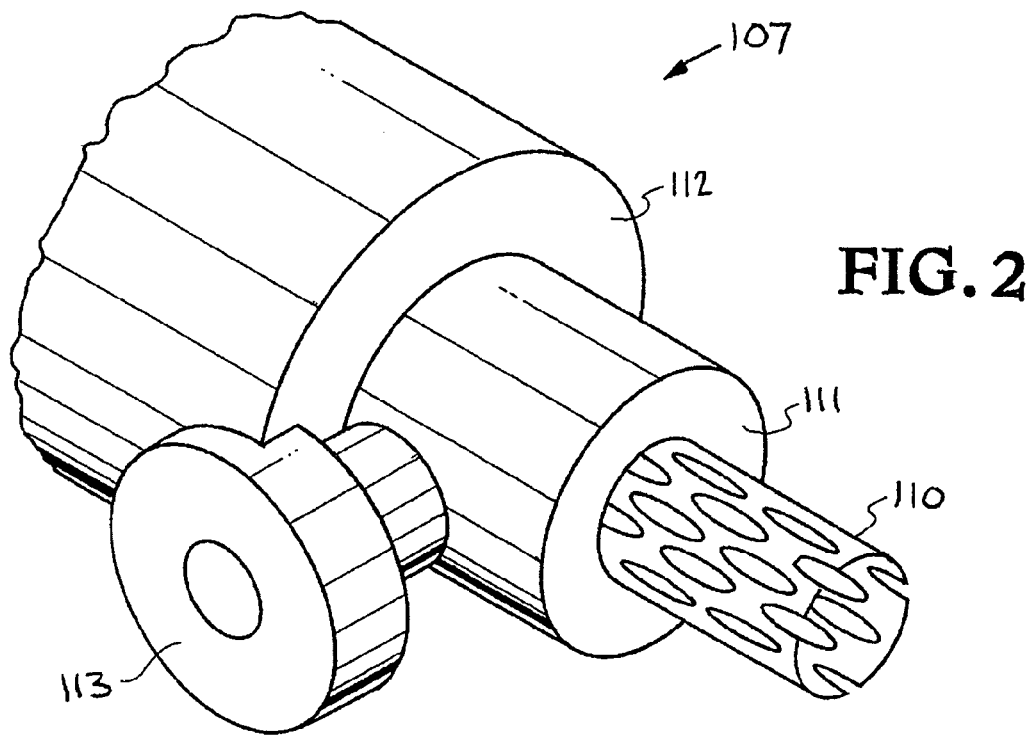
FIG. 2 shows the lipid bilayer-carbon nanotube transistor in greater detail.

Referring now to FIG. 2, the lipid bilayer-carbon nanotube transistor 107 is shown in greater detail. The lipid bilayer-carbon nanotube transistor 107 comprises a nanoelement 110, a hydrophilic cushion 111, and a lipid bilayer 112. The nanoelement is shielded with the lipid bilayer 112. The hydrophilic cushion 111 is located between nanoelement and the lipid bilayer 112. In one embodiment the nanoelement 110 is a single-wall carbon nanotube 110. In another embodiment the nanoelement 110 is a multi-wall nanotube 110. In another embodiment the nanoelement 110 is a nanowire 110. In another embodiment the nanoelement 110 is an inorganic nanowire 110.

The lipid bilayer-carbon nanotube transistor 107 includes a sensing element 113. The sensing element 113 in one embodiment is a sensing ion channel 113 connected to the lipid bilayer 112. The sensing element 113 in another embodiment is a membrane agent. The sensing element 113 in another embodiment is a natural bilayer pore. The sensing element 113 in another embodiment is a synthetic bilayer pore. The sensing element 113 is connected to the lipid bilayer 112 and the lipid bilayer 112 serves as a matrix for the sensing element 113. The nanotube 110 generates the sensor readout and the lipid bilayer 112 provides the selectivity to the analyte.

Figure 3:
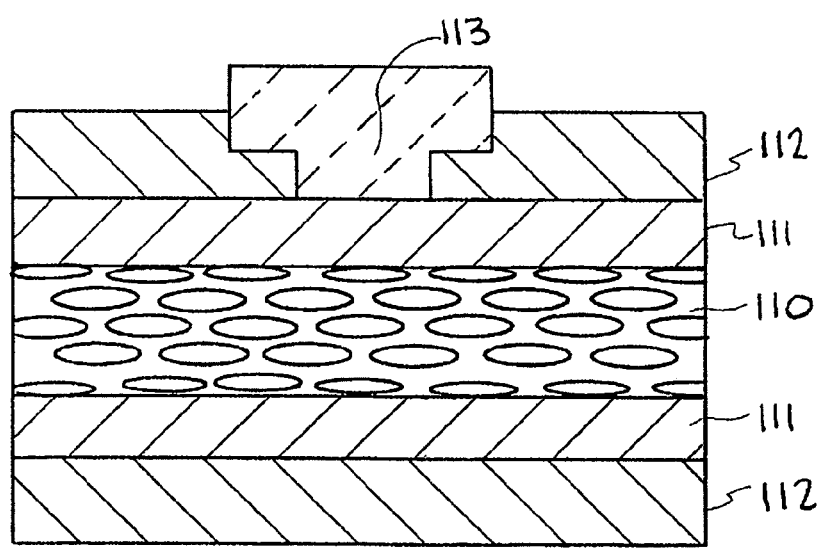
FIG. 3 is a section view of the lipid bilayer-carbon nanotube transistor.

Referring now to FIG. 3, a section view of one embodiment of the lipid bilayer-carbon nanotube transistor 107 is shown. The single-wall carbon nanotube 110 is surrounded by the hydrophilic cushion 111 and the lipid bilayer 112. The sensing element 113 is connected to the lipid bilayer 112. The lipid bilayer 112 serves as a matrix for the sensing element 113.

The structural details of the microfluidic device 100 constructed in accordance with the present invention having been described and illustrated in connection with FIGS. 1, 2, and 3, the operation of the microfluidic device 100 will now be considered. The lipid bilayer-carbon nanotube transistor 107 is suspended between source electrode 105 and drain electrode 106. The gate electrode 104 is on the bottom of the channel 101. The whole device 100 is covered with a PDMS mold with microfluidic channels.

The lipid bilayer-carbon nanotube transistor 107 provides a nanoscale biosensor for detection of pore-forming biological toxins. The lipid bilayer-carbon nanotube transistor 107 incorporates the individual carbon nanotube 110 surrounded by the lipid bilayer 112. The lipid bilayer 112 serves as a highly-selective membrane controlling access to the nanotube 110 surface. Toxins disrupt the bilayer's 112 shielding ability and changes the nanotube's 110 conductance. The lipid bilayer 112 serves as a tunable semi-permeable membrane controlling the access to the nanotube 110, and the nanotube conductance provides a readout mechanism.

The main sensing element of the system 100 is the carbon nanotube field-effect transistor (FET) 107 with a single-wall carbon nanotube 110 connecting the source 105 and drain electrodes 106. The carbon nanotube 110 is wrapped in a lipid bilayer shell 112 that houses the sensing element 113 proteins. The bilayer 112 also insulates the nanotube 110 surface from the solution providing a barrier to non-specific interactions. The lipid bilayer 112 does not contact the nanotube 110 directly; instead, it rests on a thin permeable polymer cushion 111 adsorbed on the nanotube 110.

The microfluidic device 100 will detect the presence of pore-forming bacterial toxins, since many toxins attack cells by incorporating into the membrane and forming a channel through which the other components can either enter the cell or leak out of the cell. When the microfluidic device 100 is exposed to a solution of a redox species in the absence of the toxin, the lipid bilayer 112 blocks the access to the nanotubes 110. When the toxin incorporates into the bilayer 112 and opens up a pore, the redox species are able to penetrate and bind to the nanotube 110 surface, changing the nanotube's 110 conductance and triggering the sensor readout.

The sensing principle exploits the high sensitivity of carbon nanotube transistors to gating by the external electric fields. Current flow through the ion channel 113 in the lipid shell 112 modulates the electric field in the vicinity of the nanotube 110 and produces a large modulation of the transistor current. Alterations of the transport through the ion channel 113 change transistor 107 current, which is recorded by an external circuit. The device 100 is also able to detect transport events through a single channel 101 with a signal/noise ratio of more than 100. This high efficiency is a direct consequence of two the following two advantages: (a) large gain achieved with the transistor configuration and (b) direct electrical interfacing of biological ion channels to a reporting nanostructure.

The system 100 provides a biosensor that can detect variations in ion transport through a protein pore using the lipid bilayer-carbon nanotube transistor 107. The system 100 provides superior detection efficiency by using signal amplification, and also permits straightforward integration and multiplexing. The system 100 also provides a large amount of flexibility allowing seamless integration with different types of membrane-based sensing agents. The microfluidic device 100 features high selectivity, low cost and low power consumption, and can serve as a wearable "bio-smoke alarm."

Figure 4:
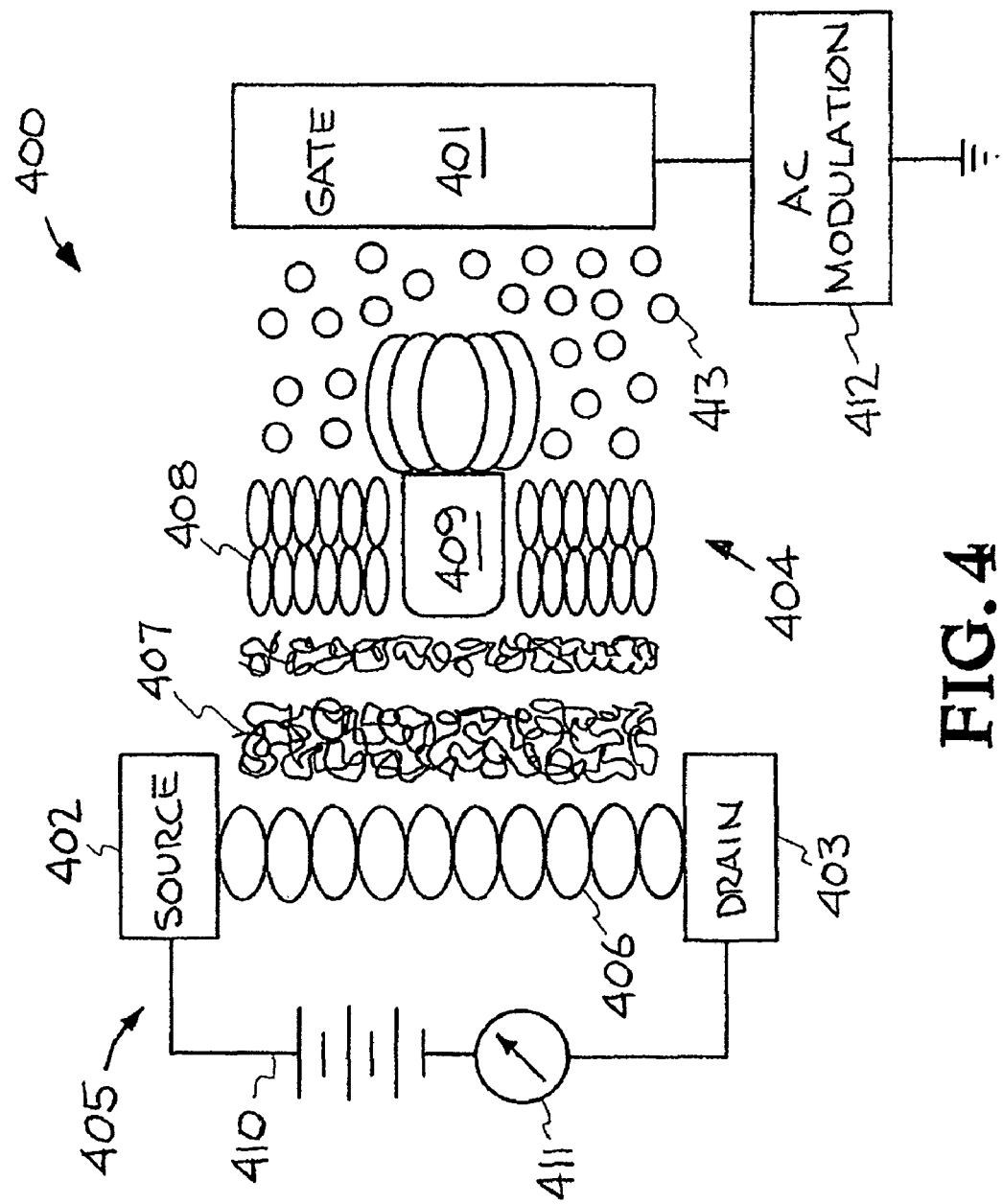
FIG. 4 illustrates the operation principle of the microfluidic device.

Referring now to FIG. 4, the operation principle of a microfluidic device constructed in accordance with the present invention is illustrated. The microfluidic device is designated generally by the reference numeral 400. The microfluidic device 400 can be briefly described as a carbon nanotube encapsulated by a lipid bilayer resting on a hydrophilic "cushion" layer. The bilayer supports the sensing ion channels and also acts as an "insulating jacket" to shield the nanotube from the solution species. This insulated carbon nanotube "wire" is suspended between microfabricated source and drain metal electrodes, forming a channel region of a field-effect transistor. The nanotube is suspended across a microfluidic channel with the third "gate" electrode running on the bottom of the channel.

The microfluidic device 400 includes a gate 401, a source 402, and a drain 403 located in a PDMS microfluidic channel 404. A lipid bilayer-carbon nanotube transistor 405 is connected to the gate 401, source 402, and drain 406 by connectors 408 and 409. The microfluidic device 400 and the lipid bilayer-carbon nanotube transistor 405 have many uses. For example, uses of the microfluidic device 400 and the lipid bilayer-carbon nanotube transistor 405 can be the uses of the devices illustrated in United States Patent Application No. 2004/0253741 by Alexander Star and George Gruner for analyte detection in liquids with carbon nanotube field effect transistor devices published Dec. 16, 2004 and United States Patent Application No. 2005/0051805 by Byong Man Kim, et al for microprocessors with improved power efficiency published Mar. 10, 2005. United States Patent Application No. 2004/0253741 by Alexander Star and George Gruner for analyte detection in liquids with carbon nanotube field effect transistor devices published Dec. 16, 2004 and United States Patent Application No. 2005/0051805 by Byong Man Kim, et al for microprocessors with improved power efficiency published Mar. 10, 2005 are incorporated herein by reference.

The main sensing element of the microfluidic device 400 is the lipid bilayer-carbon nanotube transistor 405. The lipid bilayer-carbon nanotube transistor 405 comprises a single-wall carbon nanotube 406 surrounded by a hydrophilic cushion 407 and the lipid bilayer 408. Only one side of the bilayer 408 is shown; in the device the bilayer 408, and the hydrophilic cushion 407 encircle the nanotube 408. An ion channel 409 is connected to the lipid bilayer 408. The lipid bilayer 408 serves as a matrix for the ion channel 409.

A constant small DC bias illustrated by the circuit 410 and the current meter 411 is applied between the source 402 and drain 403 electrodes of the nanotube field effect transistor 405. A small AC modulation 412 is applied to the gate electrode 401 located in the solution 413 surrounding the lipid-coated carbon nanotube 405 supporting the biological ion channel 409. Current through the ion channel 409 modulates the double layer surrounding the carbon nanotube and gates the nanotube. Changes in the source drain current are recorded by the current meter 411.

The sensing principle exploits the high sensitivity of carbon nanotube transistors to gating by the external electric fields. Current flow through the ion channel 409 in the lipid shell 408 modulates the electric field in the vicinity of the nanotube 406 and produces a large modulation of the transistor current. Alterations of the transport through the ion channel change transistor current, which is recorded by an external circuit 410. The microfluidic device 400 detects transport events through a single channel with a signal/noise ratio of more than 100. This high efficiency is a direct consequence of two advantages: platforms: (a) large gain achieved with the transistor configuration and (b) direct electrical interfacing of biological ion channels to a reporting nanostructure.

The nanotube FET 405 is gated by the electrical double layer 408 forming around the nanotube 406. The voltage drop across the double layer determines the effective gate voltage. For a given gate electrode voltage, the voltage drop across the double layer is determined by the balance of the impedances of the different circuit components: if the double layer impedance is large compared to the total impedance, most of the voltage drop occurs at the double layer. In this situation; application of an AC bias to the gate electrode will cause a large modulation of the source-drain current of the FET. If the double-layer impedance is small compared to the total impedance, there will be little to no modulation of the source-drain current.

Changes in the conductivity of the ion channel will have a large effect on the membrane impedance. When the ion channel is open, the membrane impedance is small compared to the double layer impedance, resulting in a large source-drain current modulation. When an analyte blocks the channel, membrane impedance increases and becomes larger than the double layer impedance. In this situation the voltage drop in the double layer diminishes and produces a significantly smaller modulation of transistor current.

The fabrication of functional lipid bilayers on carbon nanotube templates will now be described. Single-wall nanotubes are grown on the TEM grids using catalytic CVD synthesis to produce suspended carbon nanotubes suitable for modification process. A polymer coating is formed on these suspended carbon nanotubes by exposing them to the alternating solutions of polyanions and polycations.

Formation of a lipid bilayer around a naked carbon nanotube presents challenges. First, typical diameters of single-wall carbon nanotubes range from 1-2 nm, which is below a critical curvature of a common phospholipids bilayer. Second, the hydrophobic nanotube surface promotes the formation of a monolayer, not the bilayer that is necessary for membrane channel support. To remedy these problems Applicants placed a semi-permeable hydrophilic polymer "cushion" layer between the nanotube and the bilayer. This layer is important for a number of reasons. First, the polymer provides hydrophilic support surface for the bilayer. Second, the additional polymer layer between the nanotube and the bilayer increases the size of the structure and helps to match the size of the support to the critical bilayer curvature. Third, interactions of the lipid headgroups with the polymer "cushion" stabilize the bilayer and increase its robustness. Fourth, the polymer "cushion," which typically contains up to 50% water, lifts the membrane from the substrate and helps to maintain natural environment for inserted protein channels, which may protrude past the bilayer.

The fabrication of functional lipid bilayers on carbon nanotube or nanowire templates is described in co-pending U.S. patent application Ser. No. 11/338,512 for lipid bilayers on nano-templates filed Jan. 23, 2006 by Aleksandr Noy, Alexander B. Artyukhin, Olgica Bakajin, and Pieter Stroeve. U.S. patent application Ser. No. 11/338,512 for lipid bilayers on nano-templates filed Jan. 23, 2006 by Aleksandr Noy, Alexander B. Artyukhin, Olgica Bakajin, and Pieter Stroeve is incorporated herein by this reference.

The fabrication of the lipid bilayer on a nano-template will be summarized. The system of fabrication of the lipid bilayer on a nano-template includes various forms of nano-templates, lipid bilayers, and polymer cushions. The fabrication will be described with reference to a nanotube; however, it is to be understood that a nanowire could be used instead of the nanotube.

First, a carbon nanotube is coated with several alternating layers of oppositely charged polyelectrolytes, followed by the formation of lipid bilayer by vesicle fusion.

Single-wall nanotubes are grown on TEM grids using catalytic CVD synthesis to produce suspended carbon nanotubes suitable for modification process. A polymer coating is formed on these suspended carbon nanotubes by exposing them to the alternating solutions of polyanions and polycations.

Formation of a lipid bilayer around a naked carbon nanotube presents challenges. First, typical diameters of single-wall carbon nanotubes range from 1-2 nm, which is below a critical curvature of a common phospholipids bilayer. Second, the hydrophobic nanotube surface promotes the formation of a monolayer, not the bilayer that is necessary for membrane channel support. To remedy these problems, Applicants placed a semi-permeable hydrophilic polymer "cushion" layer between the nanotube and the bilayer. This layer is important for a number of reasons. First, the polymer provides hydrophilic support surface for the bilayer. Second, the additional polymer layer between the nanotube and the bilayer increases the size of the structure and helps to match the size of the support to the critical bilayer curvature. Third, interactions of the lipid headgroups with the polymer "cushion" stabilize the bilayer and increase its robustness. Fourth, the polymer "cushion," which typically contains up to 50% water, lifts the membrane from the substrate and helps to maintain natural environment for inserted protein channels, which may protrude past the bilayer.

The 1-D Bilayer formation is started by creating supported lipid bilayers on the "cushioned" carbon nanotubes using vesicle fusion. The multilayer polymer cushion on nanotubes with a cationic layer (PDDA or PAH) to stabilize the bilayer that contains 75% of the anionic lipid (SOPS). To enable visualization of the final structure, the vesicles incorporated a small fraction of a fluorescent lipid probe (BODIPY-PC). Scanning confocal microscope images of the resulting structures show linear fluorescent features inside the holes of the TEM grid, which correspond to the lipidcoated carbon nanotubes stretching across the grid holes. These results indicate that partial strain relief in the dimension of the nanotube axis coupled with the electrostatic attraction of the bilayer to the polymer support is sufficient to stabilize the bilayer in 1-D configuration. Incorporation of charged lipids in the membrane should reject subsequent lipid multilayer formation. One important feature of a functional lipid bilayer is the ability of the lipid molecules to diffuse along the bilayer plane.

The assembly process is started by modifying pristine suspended single-wall carbon nanotubes with five alternating polymer layers composed of strong polyelectrolytes, such as poly(diallyldimethylammonium chloride) (PDDA), sodium poly(styrenesulphonate) (PSS), and poly(allylamine hydrochloride) (PAH. critical (i.e., smallest) inner radius of the lipid bilayer is ca. 5 nm. Polyelectrolytes that form the cushion produce 1 nm thick layers at low ionic strength conditions; therefore, five polymer layers were used to match the critical curvature of the bilayer.

TEM images show that five alternating PAH/PSS layers produce smooth coating on the nanotubes over large distances, with the diameter of the final structure of 10-15 nm. Substitution of PAH to PDDA produces rougher coating of 10-30 nm in diameter. Overall, the addition of the polymer cushion made the size of the nanotubes comparable (and in some cases even larger) to the smallest reported nanoparticles (14 nm) that can support lipid bilayers.

Additional exposure to the solution of an agent is used to form the protein pore. An onomeric bacterial toxin (such as anthrax) results in the formation of the oligomeric protein pore in the bilayer membrane. It is to be understood that other agents than the anthrax toxin can be used. The agents can be biowarfare agents or health related agents. For example, the agents can include a full spectrum of biowarfare agents including bacteria, viruses and toxins, examples of which include Anthrax, Smallpox, Plague, Botulism, Tularemia, and Viral hemorrhagic fever. The agents can also include a full spectrum of health related agents including bacteria, viruses and toxins, examples of which include SARS and avian flu. A list of some of the agents is provided in Table 1 below.

TABLE 1

List of Agents

Abrin
Acids (caustics)
Adamsite (DM)
Americium-241 (AM-241

TABLE 1-continued

List of Agents

Ammonia
Anthrax (*Bacillus anthracis*)
Arenaviruses
Arsenic
Arsine (SA)
Avian flu
*Bacillus anthracis* (anthrax)
Barium
Benzene
Bioterrorism agents
Biotoxins
Blister agents/vesicants
Blood agens
Botulism
Brevetoxin
Bromine (CA)
Bromobezylcyanide (CA)
*Brucella* species (brucellosis)
Brucellosis (*Brucella* species)
*Burkholderia mallei* (glanders)
*Burkholderia pseudomallei*
BZ
Carbon Monoxide
Caustics (acids)
Cesium-137 (Cs-137)
Chemical agents
*Chlamydia psittaci* (psittacosis)
Chlorine (CL)
Chloroacetophenone (CN)
Chlorobenzylidenemalononitrile (CS)
Chloropicrin (PS)
Choking/lung/pulmonary agents
Cholera (*Vibrio cholera*)
*Clostridium botulinum* toxin
*Clostridium perfringens*
Cobalt-60 (Co-60)
Colchicine New March 15
*Coxiella burnetii* (Q fever)
Cyanide
Cyanogen chloride (CK)
Dibenzoxazepine (CR)
Digitalis New March 16
Diphosgene (DP)
Distilled mustard (HD)
Ebola virus hemorrhagic fever
*E. coli* 0157:H7 (*Escherichia coli*)
Nipah virus & hautavirus
Epsilon toxin of *Clostridium perfringens*
*Escherichia coli* 0157:H7 (*E. coli*)
Ethylene glycol
Fentanyls & other opioids
*Francisella tularensis* (tularemia)
Glanders (*Burkholderia mallei*)
Hydrofluoric acid (hydrogen Fluoride)
Hydrogen chloride
Hydrogen cyanide (AC)
Hydrogen fluoride
Incapacitating agents
Iodine-131 (1-131_
Lassa fever
Lewisite (L, L-2, L-2, L-3)
Long-acting anticoagulant
Lung/choking/pulmonary agents
Marburg virus hemorrhagic fever
Melioidosis
Methyl Bromide
Methyl Isocyanate
Mudslides & landslides
Mustard gas (H) (sulfur mustard)
Mustard/lewisite (HL)
Mustard/T
Nerve agents
Nitrogen mustard (HN-1, HN-2 HN-3

TABLE 1-continued

List of Agents

Optoids
Osmium tetroxide
Paraquat
Phosgene (CG)
Phostene oxime (CX)
Phosphine
Phosphorus, elemental, white or yellow
Plague (*Yersinia pestis*)
Plutonium-239 (pu-239
Potassium cyanide (KCN)
Psittacosis (*Chlamydia psittaci*)
Pulmonary/choking/lung agents
Q fever (*Coxiella burnetti*)
Radioisotopes (radioactive Isotopes)
Radioactive isotopes (Radioisotopes
Ricin toxin from *Ricitus communis*
*Rickeittsia prowazekii* (typlus Fever)
*Salmonella* species (salmonellosis)
*Salmonella typhi* (typhoid fever)
Salmonellosis (*Salmonella* species)
Sarin (GB)
SARS
Saxitoxin
Sesqui mustard
*Shigella* (shgellosis)
Shigellosis (*Shigella*)
Smallpox (*variola major*)
Sodium azide
Sodium cyanide (NaCN)
Sodium Monofluoroacetate
Soman (GD)
Staphylococcal enterotoxin B
Stibine
Stontium-90 (Sr-90)
Strychnine
Sulfuryl Fluoride
Sulfur mustard (H) (mustard gas)
Super warfarin
Tabun (GA)
Terodotoxin
Thallium
Trichothecene New March 17
Tularemia (*Francisella tularensis*)
Typhoid fever (*salmonella typhi*)
Typhus fever (*Rickettsia Prowazekii*)
Uranium-235 (U-235)
Uranium-238) U-238
*Varioila major* (smallpox)
Vesicants/blister agents
*Vibrio cholera* (cholera)
Viral encephalitis
Viral hemorrhagic fevers
Vomiting agents
VX
White phosphorus
*Yersinia pestis* (Plague)

Single-wall nanotubes are grown on TEM grids using catalytic CVD synthesis to produce suspended carbon nanotubes suitable for modification process. The polymer coating is formed on these suspended carbon nanotubes by exposing them to the alternating solutions of polyanions and polycations by layer-by-layer assembly. The lipid bilayer is formed by vesicle fusion. Additional exposure to the solution of an agent results in pore insertion and the formation of the protein pore in the bilayer membrane.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A nanoscale sensor apparatus for detection of biological toxins, comprising:
a base,
a microfluidic channel in said base,
a gate in said microfluidic channel,
a source in said microfluidic channel,
a drain in said microfluidic channel,
a lipid bilayer-carbon nanotube or nanowire transistor in said microfluidic channel, said lipid bilayer-carbon nanotube or nanowire transistor connected to said gate, said source, and said drain, said lipid bilayer-carbon nanotube or nanowire transistor including
a nanotube or nanowire,
a lipid bilayer around said nanotube or nanowire,
a hydrophilic cushion between said nanotube or nanowire and said lipid bilayer, wherein said hydrophilic cushion is a polymer cushion,
a sensing element connected to said lipid bilayer, and
a cover covering said microfluidic channel.

2. The sensor apparatus of claim 1 wherein said sensing element is a pore.

3. The sensor apparatus of claim 1 wherein said sensing element is a membrane agent.

4. The sensor apparatus of claim 1 wherein said sensing element is a bilayer pore.

5. The sensor apparatus of claim 1 wherein said sensing element is a natural bilayer pore.

6. The sensor apparatus of claim 1 wherein said sensing element is a synthetic bilayer pore.

7. The sensor apparatus of claim 1 wherein said sensing element is a sensing ion channel connected to said lipid bilayer.

8. The sensor apparatus of claim 1 wherein said nanotube or nanowire is a single-wall carbon nanotube.

9. The sensor apparatus of claim 1 wherein said nanotube or nanowire is a multi-wall carbon nanotube.

10. The sensor apparatus of claim 1 wherein said nanotube or nanowire is a nanowire.

11. The sensor apparatus of claim 1 wherein said nanotube or nanowire is an inorganic nanowire.

12. The sensor apparatus of claim 1 wherein said lipid bilayer is a lipid bilayer shell that surrounds said nanotube or nanowire.

13. The sensor apparatus of claim 1 wherein said sensing element is a protein pore in said lipid bilayer wherein said protein pore is sensitive to specific agents.

14. The sensor apparatus of claim 1 wherein said sensing element is a protein pore in said lipid bilayer wherein said protein pore is sensitive to a full spectrum of biowarfare agents including bacteria, viruses and toxins.

15. The sensor apparatus of claim 1 wherein said sensing element is a protein pore in said lipid bilayer wherein said protein pore is sensitive to a full spectrum of health related agents including bacteria, viruses and toxins.

16. A nanoscale biosensor apparatus for detection of biological toxins, comprising:
a base,
a microfluidic channel in said base,
a gate electrode in said microfluidic channel;

a source electrode in said microfluidic channel;
a drain electrode in said microfluidic channel;
a lipid bilayer-carbon nanotube or nanowire transistor in said microfluidic channel, said lipid bilayer-carbon nanotube or nanowire transistor including
a nanotube or nanowire operatively connected to said gate electrode, said source electrode, and said drain electrode;
a lipid bilayer around said nanotube or nanowire,
a hydrophilic cushion between said nanotube or nanowire and said lipid bilayer,
a sensing element connected to said lipid bilayer, and
a cover covering said microfluidic channel.

17. The biosensor apparatus of claim 16 wherein said nanotube or nanowire is a single-wall carbon nanotube.

18. The biosensor apparatus of claim 16 wherein said lipid bilayer is a lipid bilayer shell that surrounds said nanotube or nanowire.

19. The biosensor apparatus of claim 16 wherein said sensing element is a sensing ion channel and wherein said sensing ion channel is a protein pore in said lipid bilayer wherein said protein pore is sensitive to specific agents.

20. The biosensor apparatus of claim 16 wherein said sensing element is a sensing ion channel and wherein said sensing ion channel is a protein pore in said lipid bilayer wherein said protein pore is sensitive to a full spectrum of biowarfare agents including bacteria, viruses and toxins.

21. The biosensor apparatus of claim 16 wherein said sensing element is a sensing ion channel and wherein said sensing ion channel is a protein pore in said lipid bilayer wherein said protein pore is sensitive to a full spectrum of health related agents including bacteria, viruses and toxins.

* * * * *